United States Patent [19]

Weickmann et al.

[11] Patent Number: 5,464,770
[45] Date of Patent: Nov. 7, 1995

[54] DNA ENCODING (ASP 113) AND (LYS 46, ASP 113) THAUMATIN I

[75] Inventors: Joachim L. Weickmann; Pradip Ghosh-Dastidar, both of Los Angeles, Calif.

[73] Assignee: Xoma Corporation, Berkeley, Calif.

[21] Appl. No.: 189,250

[22] Filed: May 2, 1988

Related U.S. Application Data

[63] Continuation of Ser. No. 797,474, Nov. 13, 1985, abandoned.

[51] Int. Cl.⁶ .............................. C12N 1/19; C12N 15/29
[52] U.S. Cl. .................................. 435/254.21; 536/23.6
[58] Field of Search ............................ 435/69.1, 320, 435/256, 172.3, 252.3, 254.21; 536/27, 23.6

[56] References Cited

U.S. PATENT DOCUMENTS

| | | | |
|---|---|---|---|
| 4,657,857 | 4/1987 | Ednes et al. | 435/69.1 |
| 4,666,839 | 5/1987 | Souza | 435/91.53 |
| 4,891,316 | 1/1990 | Verrips | 435/69.1 |

FOREIGN PATENT DOCUMENTS

| | | |
|---|---|---|
| 0054330 | 6/1982 | European Pat. Off. . |
| 0054331 | 6/1982 | European Pat. Off. . |

OTHER PUBLICATIONS

Gouy et al. "Codon Usage in Bacteria: Correlation with Gene Expressivity" Nucleic Acids Research, 10, 7054–7074 (1982).

Bennetzer et al. "Codon Selection in Yeast". The Journal of Biological Chemistry, 257, 3026–3031 (1982).

Edens, et al. "Cloning of cDNA Encoding the Sweet-tasting Plant Thaumatin and its Expression in *Escherichia coli*", Gene, 18, 1–12 (1982).

Ivengar, et al., "The Complete Amino Acid Sequence Of The Sweet Protein Thaumatin I", Eur. J. Biochem. 96, pp. 193–204 (1979).

Science News, vol. 127, p. 186, Mar. 23, 1985.

Edens and van der Wel, Trends in Biotechnology, vol. 3, No. 3, pp. 61–64 (Mar. 1985).

Sensory Properties of Foods, Birch, G. C., Brennan, J. G. and Parker, L. J., eds., pp. 129–149 (1977) (Higginbotham).

*Primary Examiner*—Richard A. Schwartz
*Assistant Examiner*—Philip W. Carter
*Attorney, Agent, or Firm*—Marshall, O'Toole, Gerstein, Murray & Borun

[57] ABSTRACT

Genes are disclosed which are capable of directing the synthesis in a selected host microorganism of two thaumatin I analogues both of which have the amino acid sequence of natural thaumatin I including an aspartate amino acid residue in the 113th position from the amino terminal end of the polypeptide and one of which additionally has a lysine amino acid residue substituted for asparagine in the 46th position from the amino terminal end.

3 Claims, No Drawings

DNA ENCODING (ASP 113) AND (LYS 46, ASP 113) THAUMATIN I

This application is a continuation of application Ser. No. 797,474, filed Nov. 13, 1985, now abandoned.

BACKGROUND

The present invention relates generally to the manipulation of genetic materials and more particularly to the manufacture of specific DNA sequences useful in recombinant procedures to secure the production of analogs of a polypeptide identified as natural thaumatin I which include an aspartic acid residue in the 113th position from the amino terminal end of the polypeptide and may further include a lysine residue at the 46th position.

Thaumatin is an extremely sweet-tasting protein produced in the arils of the fruit of the African shrub *Thaumatococcus daniellii* Benth. The fruit traditionally has been used in West Africa as a sweetener of palm wine, corn, bread, and sour fruit. Thaumatin, which is about 5,000 times sweeter than sucrose on a weight basis, is produced in at least five forms: thaumatins I, II, a, b and c. These proteins, named in the order of elution from an ion exchange column [Higgenbotham, et al., *in Sensory Properties of Foods* (Birch, et al., eds.), London: Applied Sciences, pp. 129–149 (1977)], have molecular weights of approximately 22 kilodaltons. Thaumatins I and II are nearly identical proteins, each consisting of a single unmodified polypeptide chain, 207 amino acid residues in length.

Thaumatins I and II are non-toxic proteins, are low-calorie and non-cariogenic, and elicit profound sweet taste responses suggesting a stable interaction between these proteins and human taste receptors. Therefore, thaumatin has potential for use as a sugar substitute, food additive, a sweetness receptor probe and a tool for further elucidation of the taste response.

A plentiful supply of pure thaumatin is required to utilize the protein as a possible food additive and research tool. Because the thaumatin plant requires a tropical climate and insect pollination for successful fruit propagation, there are considerable difficulties involved in greenhouse cultivation of the fruit.

Iyengar disclosed an amino acid sequence for thaumatin I which is shown in Table I below [Iyengar, et al., *Eur. J. Biochem.*, 96, 193–204 (1979)].

TABLE 1

```
    1                                                              10
NH2—Ala—Thr—Phe—Glu—Ile—Val—Asn—Arg—Cys—Ser—Tyr—Thr—Val—

20
Trp—Ala—Ala—Ala—Ser—Lys—Gly—Asp—Ala—Ala—Leu—Asp—Ala—Gly—

30                                                      40
Gly—Arg—Gln—Leu—Asn—Ser—Gly—Glu—Ser—Trp—Thr—Ile—Asn—Val—

50
Glu—Pro—Gly—Thr—Asn—Gly—Gly—Lys—Ile—Trp—Ala—Arg—Thr—Asp—

60
Cys—Tyr—Phe—Asp—Asp—Ser—Gly—Ser—Gly—Ile—Cys—Lys—Thr—Gly—

70                                              80
Asp—Cys—Gly—Gly—Leu—Leu—Arg—Cys—Lys—Arg—Phe—Gly—Arg—Pro—

90
Pro—Thr—Thr—Leu—Ala—Glu—Phe—Ser—Leu—Asn—Gln—Tyr—Gly—Lys—

100                                                110
Asp—Tyr—Ile—Asp—Ile—Ser—Asn—Ile—Lys—Gly—Phe—Asn—Val—Pro—

120
Met—Asn—Phe—Ser—Pro—Thr—Thr—Arg—Gly—Cys—Arg—Gly—Val—Arg—

130
Cys—Ala—Ala—Asp—Ile—Val—Gly—Gln—Cys—Pro—Ala—Lys—Leu—Lys—

140                                                150
Ala—Pro—Gly—Gly—Gly—Cys—Asn—Asp—Ala—Cys—Thr—Val—Phe—Gln—

160
Thr—Ser—Glu—Tyr—Cys—Cys—Thr—Thr—Gly—Lys—Cys—Gly—Pro—Thr—

170                                                180
Glu—Tyr—Ser—Arg—Phe—Phe—Lys—Arg—Leu—Cys—Pro—Asp—Ala—Phe—

190
Ser—Tyr—Val—Leu—Asp—Lys—Pro—Thr—Thr—Val—Thr—Cys—Pro—Gly—

200                         207
Ser—Ser—Asn—Tyr—Arg—Val—Thr—Phe—Cys—Pro—Thr—Ala—COOH
```

The amino acid sequence for thaumatin II has been deduced from its nucleotide sequence [Edens, et al., *Gene*, 18, 1–12 (1982)] and a gene for thaumatin II has been cloned from messenger RNA-derived cDNA. The amino acid sequences of thaumatin I and thaumatin II are very similar and their amino acid sequences differ in only five positions according to the reports of Edens, et al. and Iyengar, et al. The five amino acids in the thaumatin II sequence which differ from those reported by Iyengar, et al. for the natural thaumatin I sequence are the following: lysine instead of asparagine at residue 46; arginine instead of serine at residue 63; arginine instead of lysine at residue 67; glutamine instead of arginine at residue 76; and aspartic acid instead of asparagine at residue 113. Sequence analysis also indicated that thaumatin II is initially translated as a precursor form, preprothaumatin, with both a 22 residue amino-terminal extension and an acidic, six-amino acid carboxy terminal tail. The amino terminal peptide was postulated as a secretion signal based on its hydrophobic character and a compartmentalization role was hypothesized for the carboxy terminal extension.

A great deal of work has been directed toward study of the thaumatin family of polypeptides and much effort has been directed toward the manipulation of genetic materials for the microbial production of thaumatin. The Edens, et al. reference cited above notes that a polypeptide having the native sequence of preprothaumatin II has been microbially produced. More specifically, the reference and European Patent Application Nos. 54,330 and 54,331 disclose cDNA sequences coding for native mature thaumatin II and preprothaumatin II and also disclose cloning vehicles comprising the DNA sequences for use in transformation in microorganisms.

While there exist no reports of the isolation of a gene encoding thaumatin I from natural sources (e.g., by genomic or cDNA cloning) work has also been directed toward microbial synthesis of the thaumatin I polypeptide as identified by Iyengar, et al. In co-owned, pending U.S. patent application Ser. No. 540,634 filed Oct. 11, 1983, the disclosure of which is herein incorporated by reference, techniques for the synthesis of manufactured genes coding for the amino acid sequence of thaumatin I as identified by Iyengar, et al. were disclosed, as were DNA microorganism transformation vectors, fusion genes, transformed microorganisms, the processes for expressing the manufactured gene and for securing the polypeptide product produced thereby. Specific manufactured genes of the application incorporated a number of codons "preferred" for expression in yeast host cells.

In U.S. patent application Ser. No. 540,634, procedures are also disclosed whereby the thaumatin II coding sequence could be constructed by primer-directed mutagenesis and fragment excision/religation techniques to a manufactured gene encoding the Iyengar, et al. thaumatin I sequence. Three amino acid changes ($Asn^{46}$ to $Lys^{46}$, $Ser^{63}$ to $Arg^{63}$ and $Lys^{67}$ to $Arg^{67}$) could be accomplished in a single mutagenesis procedure with two primers. The conversion from arginine to glutamine at residue number 76 could be performed in a separate mutagenesis procedure. Still another mutagenesis procedure would be required to effect the change from asparagine to aspartic acid at residue number 113. Alternatively, the changes in amino acid residues 46, 63, 67 and 76 could be effected by synthesis of four oligonucleotide fragments which would be duplexed, polymerized and digested to replace the KpnI and EcoRI duplex of the sequence in pING301. The change at residue 113 would nevertheless require an in vitro mutagenesis procedure. U.S. patent application Ser. No. 540,634 also suggests the manufacture of thaumatin analogs.

BRIEF SUMMARY

Provided by the present invention are manufactured genes capable of directing synthesis in a selected host microorganism of polypeptides having the amino acid sequence of [$Asp^{113}$] thaumatin I or [$Lys^{46}$, $Asp^{113}$] thaumatin I, i.e. containing the continuous sequence of amino acid residues of natural thaumatin I as reported by Iyengar, et al. except for an aspartate amino acid residue substituted for asparagine in the 113th position from the amino terminal end of the polypeptide and optionally a lysine amino acid residue substituted for asparagine in the 46th position. In preferred forms of the manufactured genes, the base sequences include one or more codons specifying the same amino acid on the basis of preferential expression characteristics of the codon in a projected host microorganism, e.g., *Escherichia coli*, *Saccharomyces cerevisiae*. Other preferred forms of manufactured genes include those wherein: (1) a codon specifies an additional amino acid the polypeptide synthesized (e.g., an initial methionine residue) which facilitates direct expression in *E. coli* microorganisms and/or yeast microorganisms; or (2) at least one termination codon at the end of the manufactured gene to insure proper termination of the polypeptide.

In practice of the invention to generate polypeptide products, DNA sequences, including manufactured genes, are inserted into a viral or circular plasmid DNA vector to form a hybrid vector and the hybrid vectors are employed to transform host microorganisms such as bacteria (e.g., *E. coli*) or yeast cells (e.g., *S. cerevisiae*). Vectors may also be supplied with appropriate promoter/regulator DNA sequences, allowing for controlled expression in the host microorganism. The transformed microorganisms are thereafter grown under appropriate nutrient conditions and express the polypeptide products of the invention.

Other aspects and advantages of the present invention will be apparent upon consideration of the following, detailed description thereof.

DETAILED DESCRIPTION

As employed herein, the term "manufactured" as applied to a DNA sequence or gene shall designate a product either totally chemically and enzymatically synthesized by assembly of nucleotide bases or derived from the biological replication of a product thus synthesized. As such, the term is exclusive of products "synthesized" by cDNA methods or genomic cloning methodologies which involve starting materials which are initially of biological origin.

The following abbreviations shall be employed herein to designate amino acids: Alanine, Ala; Arginine, Arg; Asparagine, Asn; Aspartic acid, Asp; Cysteine, Cys; Glutamine, Gln; Glutamic acid, Glu; Glycine, Gly; Histidine, His; Isoleucine, Ile; Leucine, Leu; Lysine, Lys; Methionine, Met; Phenylalanine, Phe; Proline, Pro; Serine, Ser; Threonine, Thr; Tryptophan, Trp; Tyrosine, Tyr; Valine, Val. The following abbreviations shall be employed for nucleotide bases: A for adenine; G for guanine; T for thymine; U for uracil; and C for cytosine.

For ease of understanding of the present invention, Table I below provides a tabular correlation between the 64 alternate triplet nucleotide base codons of DNA and the 20 amino acids and translation termination ("stop") function specified thereby.

TABLE 2

| FIRST POSITION | SECOND POSITION | | | | THIRD POSITION |
|---|---|---|---|---|---|
| | T | C | A | G | |
| T | Phe | Ser | Tyr | Cys | T |
| | Phe | Ser | Tyr | Cys | C |
| | Leu | Ser | Stop | Stop | A |
| | Leu | Ser | Stop | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val | Ala | Glu | Gly | G | fluorescamine solution, comprising 10 mg fluorescamine dissolved in 1 ml of pyridine and 100 ml acetone, which reacts with the primary amines of the polypeptides to produce intense fluorescence. The two dimensional thin layer electrophoresis/chromatography maps of the tryptic digests of plant thaumatin I and plant thaumatin II expectedly differed with respect to the positions of several peptides. These differences were confirmed by amino acid sequence analysis to correspond to the differences in amino acid residues between the two proteins. Unexpectedly, the two dimensional maps of the tryptic digests of plant thaumatin I and recombinant yeast produced thaumatin I were found to differ. In general, the relative two-dimensional positions of most of the tryptic peptides from both plant thaumatin I and recombinant thaumatin I were superimposable. One major difference in peptide mobility was observed when peptide maps of the two proteins were compared. The unusual peptide from each chromatogram was eluted with 1N HCl, lyophilized to dryness, and the sequence determined using an Applied Biosystems Model 470A Protein Sequencer. The following sequences were deduced:

TABLE 3

Plant Thaumatin I
$NH_2$—Gly—Phe—Asn—Val—Pro—Met—Asp—Phe—Ser—Pro—Thr—Thr—Arg—COOH Recombinant Thaumatin I
$NH_2$—Gly—Phe—Asn—Val—Pro—Met—_Asn_—Phe—Ser—Pro—Thr—Thr—Arg—COOH

EXAMPLE 1

In this example, 1 mg samples of isolated plant thaumatin I, plant thaumatin II and recombinant yeast produced thaumatin I produced according to the method of crowned U.S. patent application Ser. No. 540,634 were reduced and carboxymethylated to irreversibly block all sulfhydryl groups. The samples were reduced for 2 hours at 37° under nitrogen with a ten-fold molar excess of dithiothreitol (DTT) over total protein-SH in 9M urea, 0.1 mM EDTA, 0.1M tris HCl, pH 8.0. After two hours, the protein sulfhydryl groups were quantitatively labelled in the dark for 30 minutes with excess iodoacetic acid. The reaction was quenched by adding excess β-mercaptoethanol and the modified proteins were dialyzed against distilled water, lyophilized to dryness and subjected to tryptic digestion. Each 1 mg sample was dissolved in 1 ml of 50 mM ammonium bicarbonate (pH 8.0–8.4) and digested with 25–40 µg of TPCK trypsin. The mixtures were incubated at 37° C. for 12 hours. The trypsin acts to cleave the polypeptide chain on the carboxy terminal side of its lysine and arginine amino acid residues. 100 µg aliquots were removed and lyophilized to dryness.

The dried aliquots were then dissolved in 10 µl of electrophoresis buffer comprising 100 parts by volume pyridine, 8 parts by volume acetic acid and 892 parts water. Samples were spotted onto the middle of thin layer chromatography plates 3 cm from the bottom with electrophoresis conditions of 400 volts applied for 120 minutes with tap water cooling. After electrophoresis, the chromatography plates were allowed to air dry overnight and were then developed with a chromatography buffer comprising 100 parts by volume butanol, 15 parts by volume acetic acid and 38 parts by volume water. Ascending chromatography was carried out at room temperature for four hours and the plates were then dried by air.

After the plates were dry, they were sprayed with a

EXAMPLE 2

In this example, 50 ng samples of the tryptic digests of reduced and carboxymethylated plant thaumatin I, plant thaumatin II, and recombinant yeast produced thaumatin I according to the method of Example 1 were analyzed by reverse phase high performance liquid chromatography (HPLC) using an Altex C-18 gel column. Tryptic fragments were eluted with an increasing gradient (3–50%) of acetonitrile over a period of 60 minutes. After 60 minutes, the acetonitrile gradient was increased from 50% to 100% over the course of 5 minutes and the column was then washed with 100% acetonitrile for 10 minutes before the concentration was reduced to 0% acetonitrile. Approximately 15 major peaks were identified in the profiles of all of the thaumatin samples. The elution profiles of plant thaumatin I and plant thaumatin II were very similar with the exception of minor differences attributable to the known differences in amino acid residues between the two. The elution profiles of plant thaumatin I and recombinant yeast produced thaumatin I were also very similar with but one exception. The 15th major peak in plant thaumatin I which eluted at 32% acetonitrile was shifted in recombinant yeast produced thaumatin I to 29.9%.

EXAMPLE 3

In this example, the tryptic peptide which eluted in the 15th major peak (at 32% acetonitrile) from plant thaumatin I in Example 2 was analyzed to determine its amino acid sequence using an Applied Biosystems Model 470A Protein Sequencer. Three µg of a spin vacuum dried sample of the 15th tryptic peptide was resuspended with 35 µl of 100% trifluoroacetic acid. Analyses of the peptide sequence of the plant thaumatin I and of the recombinant yeast produced thaumatin I fraction eluting at 29.9% acetonitrile confirmed the sequences provided in Table 3 of Example 2.

The tryptic peptide isolated from the plant thaumatin I corresponds, with one exception, to the twelfth tryptic peptide of the Iyengar, et al. published sequence for plant thaumatin I starting at amino acid residue 107 and continuing to amino acid residue 119. The amino acid residue in position number 7 of the plant thaumatin tryptic peptide is aspartic acid (Asp) while that identified by Iyengar, et al. is asparagine (Asn).

EXAMPLE 4

In this example, samples of plant thaumatin I obtained from Sigma Chemical Co. and another unidentified plant thaumatin analogue were digested and analyzed by reverse phase high performance liquid chromatography (HPLC) according to the technique of Example 2. The elution profiles of the plant thaumatin I and the plant thaumatin analogue differed with respect to one fragment. The fragment was that extending from the 30th to the 49th amino acid residues of the thaumatin I polypeptide. In the thaumatin I polypeptide the 46th residue was asparagine while that in the analogue was identified to be lyisine. The amino acid residue in the 113th position was identified as aspattic acid in both polypeptides.

EXAMPLE 5

An entire synthetic gene for thaumatin I was assembled through use of 28 principal oligonucleotide fragments (designated 1a, 1b, 2a, 2b, etc., in Table 4, below) having a length of 25 to 39 residues and designed to encode the amino acid sequence of thaumatin I published by Iyengar, et al., supra. The gene contained codons corresponding to the "favored triplets" of *S. cerevisiae* based on the Bennetzen, et al., J. Biol. Chem., 257, 3026–3031 (1982), study of highly expressed yeast gene sequences.

TABLE 4

| | |
|---|---|
| 1a | 5'-(CCAG) TGATC ATG GCT ACC TTC GAA ATC GTT A-3' |
| 1b | 3'-CTT TAG CAA TTG TCT ACA AGA ATG TGA CAA A-5' |
| 2a | 5'-GG GCT GCT GCT TCC AAG GGT GAC GCT G-3' |
| 2b | **** 3'CA CTG CGA CGA AAC CTG CTCGAG(TTCC)-5' |
| 3a | **** 5'-(CCTT)GAGCTC C GGT GGT AGA CAA TTG A-3' |
| 3b | 3'-CT GTT AAC TTG AGA CCA CTT AGG AC-5' |
| 4a | 5'-G ACC ATC AAC GTC GAA CCA GGT AAC AA-3' |
| 4b | 3'-T CCA TTG TTG CCA CCA TTC TAG A (TTCC)-5' |
| 5a | 5'-(CCTT) AG ATC TGG GCT AGA ACC GAC TGT TAC TTC GAT G-3' |
| 5b | 3'-TG AAG CTA CTG AGA CCA AGG CCA TAG ACA TTC TGA CC-5' |
| 6a | 5'-T GAC TGT GGT GGT TTG TTG AGA TGT AAG AGA TTC GGT-3' |
| 6b | 3'-TCT AAG CCA TCT GGT GGT TGG TGA AAC CGA CTT AAG (TCT)-5' |
| 7a | 5'-(GCT) GAA TTC TCT TTG AAC CAA TAC GGT AAG GAC-3' |
| 7b | 3'-CCA TTC CTG ATG TAG CTA TAG AGG TTG TAG TTC-5' |
| 8a | 5'-GGT TTC AAC GTT CCA ATG AAC TTC TCT CCA ACC-3' |
| 8b | 3'-AGA GGT TGG GCA TCT CCA ACA TCT **** CCTCGAG (TTCC)-5' |

TABLE 4-continued

| | |
|---|---|
| 9a | **** 5'-(TTCC)GAGCTC GTC AGA TGT GCT GCT GAC ATC-3' |
| 9b | 3'-CTG TAG CAA CCA GTT ACA GGT CGA TTC GAA (CCCTT)-5' |
| 10a | 5'-(TTCCT) AAG CTT AAG GCT CCA GGT GGT GGT TGT AAC-3' |
| 10b | 3'-CCA ACA TTG CTG CGA ACA TGG CAA AAG GTT TGA-5' |
| 11a | 5'-TCC GAA TAC TGT TGT ACC ACT GGT AAG TGT GGT-3' |
| 11b | 3'-TTC ACA CCA GGT TGG CTT ATC AGA TCT (CCTT)-5' |
| 12a | 5'-(TTCC) TCT AGA TTC TTC AAG AGA TTG TG-3' |
| 12b | **** 3'-C TCT AAC ACA GGT CTG CTCGAG(TTC)-5' |
| 13a | **** 5'-(TTCC)GAGCTC T TTC TCC TAC GTC TTG GAC AA-3' |
| 13b | 3'-G AAC CTG TTC GGT TGA TGG CAG TGA ACA GGT-5' |
| 14a | 5'-GGT TCT TCC AAC TAC AGA GTT ACC TTC TCT C-3' |
| 14b | 3'-GG AAG ACA GGT TGA CGG ATT ACT GAG CTC (CCTT)-5' |

As often as possible, codons were employed to introduce unique restriction enzyme recognition sites at regular intervals into the sequence. In two cases, rarely used codons were required to form recognition sites at desired locations, i.e., the codon for glycine at residue 123 in Table 8, infra, is GGC, rather than the "favored triplet" GGT, and the codon for leucine at residue 138 is CTT, rather than the "favored triplet" TTG. As an aid to assembly of the entire gene from intermediate double-stranded sequences, oligonucleotides were designed to allow for the presence in intermediate structures of three SstI sites within (and interruptive of) the protein coding region. The "extra" bases needed to develop these sites are within parentheses and noted by asterisks in Table II. As discussed infra, these bases are deleted from the gene in the course of final assembly. Additional bases within parentheses in Table II are included to insure efficient digestion of duplexes formed and are not part of the intermediate one-pair or two-pair segments or the final gene.

The 28 oligonucleotides corresponding to regions of the thaumatin I sequence were synthesized by the phosphotriester method on a solid support, with dimer couplings, and purified by high performance liquid chromatography according to Ito, et al., *Nucleic Acids Res.*, 10, 1755–1769 (1982). In some cases the Ito, et al. process was modified to include initiating the assembly of each oligonucleotide from 30 mg nucleoside-bound (0.10–0.17 mmole/g) polystyrene resin (1% cross-linked) rather than the usual 50–60 mg resin. The average yield of oligonucleotide per dimer coupling was 90% to 99%.

The following example illustrates the manipulations performed on the oligonucleotides to assemble them into duplexes and combine duplexes into gene segments for cloning into a vector.

EXAMPLE 6

As summarized in Table 5, below, the 28 oligonucleotides synthesized in Example 5 were assembled into partial duplexes containing a sense and antisense strand with a 9 or 10 base pair overlap at the 3' terminus of each oligonucleotide.

observed. Therefore, to direct the proper annealing, a third "c" oligonucleotide was synthesized which was complementary to a region of one of the oligonucleotides and contigu-

TABLE 5

| Oligo-nucleotides Combined | Oligo-nucleotide 5' End-Labelled | Restriction Endonuclease | "c" Sequence Employed |
| --- | --- | --- | --- |
| 1a and 1b | 1b | BclI | — |
| 2a and 2b | 2a | SstI | — |
| 3a and 3b | 3b | SstI | — |
| 4a and 4b | 4a | BglII | — |
| 5a and 5b | 5b | BglII | — |
| 6a and 6b | 6a | EcoRI | — |
| 7a and 7b | 7b | EcoRI | — |
| 8a and 8b | 8a | SstI | 5'-ACTAGAGGTTGTAGA-3' |
| 9a and 9b | None | SstI HindIII | 5'-AGCAGCACATCTGACGA-3' |
| 10a and 10b | 10b | HindIII | — |
| 11a and 11b | 11a | XbaI | — |
| 12a and 12b | None | SstI | — |
| 13a and 13b | 13b | SstI | 5'-GCCAACTACCGTCACTT-3' |
| 14a and 14b | 14a | XhoI | 5'-CAACTGCCTATTGACTCGA-3' |

The oligonucleotide of each pair which was to participate in a blunt-end ligation was 5'-end labelled. Labelling was performed with [$^{32}$P] transfer from [γ-$^{32}$P]ATP by T4 polynucleotide kinase according to the procedure of Sgaramella, et al., *J. Mol. Bio.*, 72, 427–444 (1972) and complete phosphorylation was effected by subsequent ATP (0.5 mm) addition. All oligonucleotide pairs were labelled in this fashion except oligonucleotide pairs 9 and 12. These oligonucleotide pairs were subsequently to be digested at both ends, so prior 5' phosphorylation would not facilitate visualization of a doubly-digested duplex. For these oligonucleotide pairs radiolabelling was performed with [α-$^{32}$P]dATP during the elongation.

The labelled oligonucleotide was mixed with an equal amount of its unlabelled partner (50–200 ng), heated to 90° C. for one minute and slowly cooled to 23° C. to allow proper annealing. Oligonucleotides were extended at 23° C. for one hour with one unit DNA polymerase I (Klenow), or 24 units reverse transcriptase and 0.5 mM deoxynucleoside triphosphates. The enzyme was subsequently denatured and the mixture desalted.

Each oligonucleotide pair was digested overnight with the appropriate restriction endonuclease and the enzyme denatured. Analysis of the digestion mixture was carried out by autoradiography of a nondenaturing 15% polyacrylamide gel and the desired band excised. This fragment was eluted from the gel by diffusion at 37° C. overnight and concentrated and further purified by passage through a BND-cellulose mini-column [Rossi, J., et al., *J. Mol. Biol.*, 128, 21–47 (1979)].

For oligonucleotide pairs 8a plus 8b, 9a plus 9b, 13a plus 13b, and 14a plus 14b, self-annealing of fragments was observed. Therefore, to direct the proper annealing, a third "c" oligonucleotide was synthesized which was complementary to a region of one of the oligonucleotides and contiguous with the overlap region. This "c" oligonucleotide acted as an extension of the overlap region and was elongated to produce the desired duplex.

In cases where a "c" oligonucleotide was required, the above protocol with several modifications was followed. The scale for duplex synthesis was increased due to the lower yields. 250 ng to 1 µg of each oligonucleotide (a and b) was used and a two- to six-fold molar excess of the phosphorylated "c" oligonucleotide was added. The three oligonucleotides were mixed after labelling and phosphorylation of the appropriate oligonucleotide(s), denatured, annealed and extended as before. After restriction enzyme digestion the duplex was purified by 15% polyacrylamide gel electrophoresis, but at a very low current to prevent melting of the extended "c" oligonucleotide from the duplex. After digestion this oligonucleotide is bound to the duplex by the hydrogen bonding of 15 base pairs (duplexes 9 and 14), 17 base pairs (duplex 8) or 23 base pairs (duplex 13). Polymerization of approximately 30% of the labelled oligonucleotide was achieved thereby.

As indicated in Table 6, below, extended and digested duplexes 9 (from oligonucleotides 9a and 9b) and 12 (from oligonucleotides 12a and 12b) forming a one-duplex segment had restriction endonuclease enzyme sticky ends at both termini. The extended duplexes designed to form a two-duplex segment (duplexes 1 and 2, 3 and 4, 5 and 6, 7 and 8, 10 and 11, 13 and 14) had a sticky end at one terminus and a blunt end at the other.

TABLE 6

| Pair | Sequence |
| --- | --- |
| 1 | BclI<br>5'-GATC ATG GCT ACC TTC GAA ATC GTT AAC AGA TGT TCT TAC ACT GTT T-3'<br>3'-TAC CGA TGG AAG CTT TAG CAA TTG TCT ACA AGA ATG TGA CAA A-5' |
| 2 | SstI<br>5'-GG GCT GCT GCT TCC AAG GGT GAC GCT GCT TTG GAC GAGCT-3'<br>3'-CC CGA CGA CGA AGG TTC CCA CTG CGA CGA AAC CTG C-5' |

TABLE 6-continued

| Pair | Sequence |
|---|---|
| 3 | SstI<br>5'-CC GGT GGT AGA CAA TTG AAC TCT GGT GAA TCC TG-3'<br>3'-TCGAGG CCA CCA TCT GTT AAC TTG AGA CCA CTT AGG AC-5' |
| 4 | BglII<br>5'-G ACC ATC AAC GTC GAA CCA GGT AAC AAC GGT GGT AA-3'<br>3'-C TGG TAG TTG CAG CTT GGT CCA TTG TTG CCA CCA TTC TAG-5' |
| 5 | BglII<br>5'-G ATC TGG GCT AGA ACC GAC TGT TAC TTC GAT<br>3'-ACC CGA TCT TGG CTG ACA ATG AAG CTA<br><br>GAC TCT GGT TCC GGT ATC TGT AAG ACT GG-3'<br>CTG AGA CCA AGG CCA TAG ACA TTC TGA CC-5' |
| 6 | 5'-T GAC TGT GGT GGT TTG TTG AGA TGT AAG AGA TTC<br>3'-A CTG ACA CCA CCA AAC AAC TCT ACA TTC TCT AAG<br><br>EcoRI<br>GGT AGA CCA CCA ACC ACT TTG GCT G-3'<br>CCA TCT GGT GGT TGG TGA AAC CGA CTT AA-5' |
| 7 | EcoRI<br>5'-AA TTC TCT TTG AAC CAA TAC GGT AAG GAC TAC ATC GAT ATC TCC AAC ATC AAG-3'<br>3'-G AGA AAC TTG GTT ATG CCA TTC CTG ATG TAG CTA TAG AGG TTG TAG TTC-5' |
| 8 | SstI<br>5'-GGT TTC AAC GTT CCA ATG AAC TTC TCT CCA ACC ACT AGA GGT TGT AGA GGAGCT-3'<br>3'-CCA AAG TTG CAA GGT TAC TTG AAG AGA GGT TGG GCA TCT CCA ACA TCT CC-5' |
| 9 | SstI HindIII<br>5'-C GTC AGA TGT GCT GCT GAC ATC GTT GGT CAA TGT CCA GCT A-3'<br>3'-TCGAG CAG TCT ACA CGA CGA CTG TAG CAA CCA GTT ACA GGT CGA TTC GA-5' |
| 10 | HindIII<br>5'-AG CTT AAG GCT CCA GGT GGT GGT TGT AAC GAC GCT TGT ACC GTT TTC CAA ACT-3'<br>3'-A TTC CGA GGT CCA CCA CCA ACA TTG CTG CGA ACA TGG CAA AAG GTT TGA-5' |
| 11 | XbaI<br>5'-TCC GAA TAC TGT TGT ACC ACT GGT AAG TGT GGT CCA ACC GAA TAC T-3'<br>3'-AGG CTT ATG ACA ACA TGG TGA CCA TTC ACA CCA GGT TGG CTT ATC AGA T-5' |
| 12 | XbaI SstI<br>5'-CT AGA TTC TTC AAG AGA TTG TGT CCA GAC GAGCT-3'<br>3'-CT AAG AAG TTC TCT AAC ACA GGT CTG C-5' |
| 13 | SstI<br>5'-CT TTC TCC TAC GTC TTG GAC AAG CCA ACT ACC GTC ACT TGT CCA-3'<br>3'-TCGAGA AAG AGG ATG CAG AAC CTG TTC GGT TGA TGG CAG TGA ACA GGT-5' |
| 14 | XhoI<br>5'-GGT TCT TCC AAC TAC AGA GTT ACC TTC TGT CCA ACT GCC TAA TCA C-3'<br>3'-CCA AGA AGG TTG ATG TCT CAA TGG AAG ACA GGT TGA CGG ATT ACT GAG CT-5' |

The following example is directed to the preparation of three intermediate vectors, each containing a sub-assembly portion of a completely assembled manufactured gene for thaumatin I.

EXAMPLE 7

Three portions of the synthetic thaumatin gene were constructed concurrently in three different pBR322 derived vectors. Portion A consisted of extended duplexes 1 and 2, 3 and 4, and 5 and 6; Portion B consisted of extended duplexes 7 and 8, 9 and 10 and 11; and Portion C consisted of duplexes 12 and 13 and 14. Plasmid pING233 was designed to receive Portion A, plasmid pING235 to receive Portion B, and plasmid pING237 to receive Portion C. As shown in Table 7 below, during construction of these plasmids new restriction enzyme sites were introduced into plasmid vector pBR322 by blunt end ligation of synthetic undecamer (11-mer) linkers and one commercially available 8-mer linker into existing restriction sites [Maniatis, et al., *Cell*, 15, 687–701 (1978)].

TABLE 7

| New Plasmid | Former pBR322 Restriction Endonuclease Enzyme Recognition Site | New Restriction Endonuclease Enzyme Recognition Site | Synthetic Linker |
|---|---|---|---|
| pING233 | BamHI | BglII | 5'-GGAGATCTCCC-3' |
| | SalI | SstI | 5'-GGCGAGCTCCCG-3' |
| | PvuII | BclI | 5'-TGATCACGCCG-3' |
| pING235 | ClaI | SstI | 5'-GGCGAGCTCCCG-3' |
| | BamHI | XbaI | 5'-GGTCTAGAGCC-3' |
| pING237 | BamHI | XbaI | 5'-GGTCTAGAGCC-3' |
| | SalI | SstI | 5'-GGCGAGCTCCCG-3' |
| | PvuII | XhoI | 5'-CCTCGAGG-3' (Collaborative Research, Inc., Waltham, MA) |

Duplexes prepared as described in Examples 5 and 6 were ligated into the appropriate vector to produce a segment. The two segments formed by only one duplex, i.e., duplex 9 and duplex 12, required double digestion of the duplex and ligation to the cohesive termini of the vector. The six segments formed by ligation of two duplexes, i.e., formed by duplexes 1 and 2, 3 and 4, 5 and 6, 7 and 8, 10 and 11, 13 and 14, were created by sticky-end ligation of each cleaved duplex to the sticky ended vector and blunt end ligation to each other.

Plasmid pING233 (0.4 pmoles) was digested with restriction endonuclease enzymes BglII and SstI and dephosphorylated with calf intestinal alkaline phosphatase. The segment formed by purified duplexes 3 and 4 (1 picomole each) were digested with the same enzymes and mixed with the vector. Ligation was carried out at 12° C. overnight with 400 units of T4 DNA ligase. This ligation mixture was used to transform *E. coli* HB101 cells. In a similar manner, the segments formed by duplexes 5 and 6 and 1 and 2, respectively, were sequentially inserted into the cloning vector containing duplexes 3 and 4, so that the resulting vector, pING249, contained Portion A of the synthetic thaumatin gene.

Plasmid pING235 was manipulated in a similar manner to insert the segments formed by duplexes 7 and 8, and 10 and 11 of Portion B of the gene. However, to clone duplex 9, further modifications in the usual protocol were required. Polymerized duplex 9 could not be digested with HindIII and thus was ligated as a duplex with one sticky and one blunt end after SstI digestion. The plasmid pING235 was digested with HindIII, filled in with DNA polymerase (Klenow) and digested with SstI to provide compatible ends for ligation of duplex 9. Thereafter the duplexes 10 and 11 and 7 and 8, respectively, were inserted to complete Portion B and form the resulting vector pING268.

Plasmid pING237, into which Portion C of the gene was to be inserted, also required modification of the usual protocol to insert the segment formed by duplexes 13 and 14. Following digestion of duplex 12 and pING237 with XbaI and SstI and ligation of duplex 12 to the cohesive termini of the vector, attempts were made to insert the segment formed by duplexes 13 and 14. Initial attempts to clone the duplexes 13 and 14 which had been cleaved with SstI and XhoI, respectively, yielded a high frequency of recombinants, all of which contained only duplex 13, sticky-end ligated at the SstI site and blunt-end ligated near the XhoI site of the vector. By inserting duplex 14 as a doubly-phosphorylated, blunt-end duplex, no XhoI nuclease-sensitive overhang was present. The vector was digested with SstI/PvuII and dephosphorylated; duplex 13 was not phosphorylated. Therefore, the vector could not reclose without the phosphorylated duplex 14. The vector containing all of the Portion C was named pING277.

The following description is directed to the screening procedures employed to ensure that proper ligation events occurred in assembly of plasmids pING256, pING270 and pING285.

To detect inversions and deletions at the point of blunt-ended ligation, a "junction-region" probe was employed for use in colony hybridization. Because the percentage destabilization produced by one base mismatch is very great and even single base deletions at the junction can be discerned very easily with a short probe [Wallace, et al., *Nucleic Acids Research*, 6, 3543–3557 (1979)], an undecamer was designed for each set which spanned the junction and was therefore complementary to the end of each contributor to the blunt-ended ligation. A probe of this length hybridizes very strongly to the correctly ligated product.

Colony hybridization was performed according to the procedures of Grunstein, et al., *PNAS-USA*, 72, 3961–3965 (1975) and Wallace, et al., *Nucleic Acids Research*, 9, 879–894 (1981) with the following modifications, Filters were prehybridized with 10× Denhardt's, 4× or 1× SSC, 0.5% Triton X-100 and 100 µg/ml herring sperm DNA at 60° C. for two hours. Synthetic junction probes were radioactively labelled with [$\gamma$-$^{32}$P]ATP as described in Sgaramella, supra. Undecamers were separated from unincorporated label by polyacrylamide gel electrophoresis. Gene fragments (25- to 39-mers) were centrifuged through a P-10 column to remove unreacted ATP. Hybridization with undecamer probes was performed at 22° C. in 4× SSC for 2 to 12 hours. The filters were subsequently washed for ten minutes in 4× SSC at the same temperature three times. Gene fragments were hybridized at 50° C. in 1× SSC and washed in 1× SSC at 40° C., for the same intervals as the undecamers.

The following description is directed to sequencing of the vectors.

Because the cloning of synthetic segments into each vector was a sequential process, the newly-inserted duplexes were sequenced to avoid error accumulation before integration of further duplexes into the same vector. Dideoxy chain termination sequencing was performed directly from linearized plasmid DNA as described in Sanger, et al., *PNAS-USA*, 74, 5463–67 (1977) and Wallace, et al., *Nucleic Acids Research*, 19, 879–894 (1981), using synthetic oligomers complementary to portions of pBR322 or gene fragments as primers. Plasmid DNA for sequencing was prepared by a mini-lysate protocol [Holmes, et al., *Anal. Biochem.*, 114, 193–197 (1981)] and rapidly purified on an RPC5 analog mini-column to remove small oligonucleotide primers [Thompson, et al., *Methods in Enzymology*, 100, 368–399 (1983)]. With pBR322 oligonucleotides (13-mers) and thaumatin oligonucleotides (25- to 39-mers) as primers, the reactions were performed at 30° C. and 37° C., respectively.

Sequence analysis of hybridization-positive colonies determined that greater than 60% of these clones contained a deletion, insertion or base change. Single nucleotide changes were most frequent and (in 90% of the cases) consisted of G to A transitions on the synthesized strand, possibly caused by dimer impurity or incomplete deblocking of G residues before annealing and polymerization.

The following example is directed to improved methods of primer directed mutagenesis employing a linearized single-stranded plasmid template to correct the several single base changes noted above.

EXAMPLE 8

An improved process for selectively altering the nucleotide sequence of a double-stranded plasmid DNA sequence having at least two unique restriction endonuclease enzyme recognition sites was developed during the course of the construction of the thaumatin genes, and involves annealing a single-stranded primer oligonucleotide containing a selected alteration to one strand of the double-stranded DNA sequence and extending the primer to form a partial complement thereof. The improvement in this mutagenesis process comprises the steps of:

(a) linearizing the double-stranded plasmid DNA sequence by restriction endonucleaseenzyme digestion at a first unique recognition site in the sequence;

(b) denaturing the linearized double-stranded DNA sequence formed in step (a) into two complementary linear single-stranded DNA sequences;

(c) annealing the primer to one of the linear single-stranded sequences formed in step (b) and extending the primer to form a partially double-stranded DNA sequence;

(d) denaturing this partially double-stranded sequence formed in step (c) into the original plasmid-derived single-stranded sequence and a primer-derived single-stranded DNA sequence;

(e) linearizing the double-stranded plasmid DNA sequence by restriction endonuclease enzyme digestion at a second unique recognition site in the sequence;

(f) denaturing the linear sequence formed in step (e) into two complementary single-stranded DNA sequences;

(g) annealing the primer-derived single-stranded DNA sequence formed in step (d) to a plasmid-derived complementary single-stranded sequence formed in step (f);

(h) recircularizing the annealed strands of step (g) into a double-stranded DNA plasmid with an alteration in one strand;

(i) transforming a host microorganism with the plasmid formed in step (h) and isolating daughter cell populations containing plasmids with the selectively altered sequence by hybridization with the primer; and (j) transforming a host microorganism with the selectively altered plasmids obtained from the hybridization of step (i).

As one example, this complementary strand mutagenesis was employed to cause an A to C transversion in the codon specifying threonine at position number 154 of the thaumatin I sequence (see Table 8, infra). The plasmid manipulated contains duplexes 9 to 11 between the SstI and XbaI sites of pBR322 derivative pING235. After digestion of the supercoiled plasmid with a restriction endonuclease enzyme, PstI, one microgram of the now-linearized plasmid was mixed with a twenty-fold molar excess of a phosphorylated mutagenic primer having the correct sequence, 5'-CAAA$^C$T-TCCGA-3'. In 25 µl polymerization buffer the linearized double-stranded plasmid was denatured and the primer reannealed as follows. The mixture was sealed in a capillary tube, incubated at 100° C. for three minutes and plunged into an ice water bath for several minutes. Prior to polymerization the mixture was pre-incubated at the reaction temperature, 12° C., for ten minutes.

Primer elongation was carried out in 0.5 mM deoxynucleoside triphosphates, 5 mM DTT and 1 unit DNA Polymerase I, Klenow Fragment at 12° C. for thirty minutes followed by 37° C. for two hours. The mixture was then heated at 100° C. for one minute to denature the polymerase and mixed with pING235, linearized by digestion with 1 µg AvaI and dephosphorylated. The reaction mixture was diluted to 100 µl, sealed in a capillary tube, heated to 100° C. for three minutes and incubated at 60° C. for two hours to reanneal the extended primer to a complementary strand. The desired hybrid contains different locations for the restriction endonuclease enzyme recognition site at which each strand was cleaved; thus, when completely annealed, a circular structure is formed. The mixture was desalted by centrifugation through P10, lyophilized and dissolved in 20 µl polymerase buffer. A complete, circular duplex was created by incubation with 400 units T4 DNA ligase, 0.5 mM deoxynucleoside triphosphates, 0.5 mMATP and 1 unit DNA Polymerase I, Klenow Fragment overnight at 12° C. After transformation of *E. coli* HB101, colonies were screened by hybridization using the primer as probe.

An alternative improved process was developed for selectively altering the nucleotide sequence of a double-stranded plasmid DNA sequence having first, second and third unique restriction endonuclease enzyme recognition sites, wherein a single-stranded primer oligonucleotide containing the selected alteration is annealed to one strand of the double-stranded DNA sequence and extended to form a partial complement thereof, and the plasmid DNA sequence to be altered is between the second and third recognition sites. The improvement comprises the steps of:

(a) linearizing the double-stranded plasmid DNA sequence by restriction endonuclease enzyme digestion at the first recognition site in the sequence;

(b) denaturing the linearized double-stranded DNA sequence formed in step (a) into two complementary linear single-stranded DNA sequences;

(c) annealing the primer to one of the linear single-stranded sequences formed instep (b) and annealing to the same linear sequence a second primer complementary to a portion of the sequence between the first and second recognition sites and extending the primers to form a partially double-stranded DNA sequence including both the second and third recognition sites;

(d) cleaving the partially double-stranded sequence formed in step (c) by restriction endonuclease digestion at the second and third restriction sites to form a double-stranded sequence which is a hybrid of a plasmid single strand and the primer extended strands;

(e) inserting the fragment formed in step (d) into the DNA plasmid to form a double-stranded plasmid including the alteration in one of its strands;

(f) transforming a host microorganism with the plasmid formed in step (e) and isolating daughter cell populations containing double-stranded plasmids with the selectively altered sequence by hybridization with the primer; and (g) transforming a host microorganism with the selectively altered plasmids obtained from the hybridization of step (f).

As one example, this fragment excision/religation mutagenesis technique was employed to correct a G to A transition in the center of the codon specifying glycine at position number 144 of the thaumatin I gene. The second primer was employed upstream from the mutagenic primer, which, when elongated, reformed the recognition site. One microgram of super-coiled plasmid containing duplexes 7–11 inserted between the EcoRI and XbaI sites of pING235 was digested to completion with restriction endonuclease enzyme PstI. This plasmid was combined with 30 ng (6 pmole) each: (a) phosphorylated mutagenic primer containing the alteration, 5'-CAACCA$^C$CACC-3'; and (b) a pBR322 primer, 5'-GTTGAAGGCTCTC-3', which is complementary to the sequence adjacent to the SalI site and primes counterclockwise. The mixture was denatured and the primers annealed as described above for the complementary strand mutagenesis. Prior to polymerization and ligation the solution was pre-incubated at the reaction temperature (12° C.) for five minutes and then the solution was adjusted as follows: 0.5 mM in each dNTP, 5 mM DTT, 1 unit DNA Polymerase I, Klenow Fragment, 0.5 mM in ATP, and 400 units T4 DNA ligase. The mixture was incubated at 12° C. overnight, the enzymes denatured and the restriction enzymes XbaI and EcoRI used to excise a portion of the newly-copied region. This was mixed with the equivalently digested, dephosphorylated pING235-derivative plasmid containing duplexes 7–11 and ligated at 12° C. overnight. The mixture was used to transform HB101 and ampicillin-resistant colonies were screened by colony hybridization using the primer containing the alteration as the probe.

The following example is directed to the final assembly of the gene from the corrected portions A, B and C of plasmids pING249, pING268 and pING277.

EXAMPLE 9

After correction of all the nucleotide errors by in vitro mutagenesis in Example 8, the SstI site (5'-GAGCTC-3') of each completed gene portion was destroyed by removal of the AGCT sequence. Each plasmid was digested to completion with SstI and adjusted to 0.5 mM in each deoxynucleotide triphosphate. Removal of the 3' single stranded end was accomplished by the addition of 1 unit of DNA Polymerase I (Klenow) and incubation of the mixture at 22° C. for 15 minutes. T4 DNA ligase was then added (400 units) and the solution placed at 12° C. overnight. The ligation mixture was used to transform HB101 and ampicillin-resistant colonies were screened for the SstI site. Following these procedures, the resulting plasmids were redesignated. pING249 became pING250; pING268 became pING270; and pING277 became pING278.

pING250 was thereafter digested with BclI enzyme and blunt-ended by S1 nuclease. A BamHI linker of sequence 5'-CGGGATCCCG-3' (New England Biolabs) was inserted between the blunt ends to generate pING256. An additional "stop" codon was introduced into pING278 by primer-directed mutagenesis to generate pING285.

The three completed portions of the gene present in plasmids pING256, pING270 and pING285 were then combined into one complete gene sequence, as set out in Table 8, below.

TABLE 8

```
BclI
                              HpaI
   -1   1                                          10
   Met  Ala  Thr  Phe  Glu  Ile  Val  Asn  Arg  Cys  Ser  Tyr  Thr  Val  Trp  Ala  Ala  Ala  Ser
        ——— 1a ———                                                              ——————— 2a
   GATC ATG GCT ACC TTC GAA ATC GTT AAC AGA TGT TCT TAC ACT GTT TGG GCT GCT GCT TCC
        TAC CGA TGG AAG CTT TAG CAA TTG TCT ACA AGA ATG TGA CAA ACC CGA CGA CGA AGG
                                                      ——— 1b ———

20                                         30
   Lys  Gly  Asp  Ala  Ala  Leu  Asp  Ala  Gly  Gly  Arg  Gln  Leu  Asn  Ser  Gly  Glu  Ser  Trp  Thr
                                              ——— 3a ———
   AAG  GGT GAC GCT GCT TTG GAC GCC GGT GGT AGA CAA TTG AAC TCT GGT GAA TCC TGG ACC
   TTC  CCA CTG CGA CGA AAC CTG CGG CCA CCA TCT GTT AAC TTG AGA CCA CTT AGG ACC TGG
                   ——— 2b ———                        ——— 3b ———

KpnI              BglII
        40                                         50
   Ile  Asn  Val  Glu  Pro  Gly  Thr  Asn  Gly  Gly  Lys  Ile  Trp  Ala  Arg  Thr  Asp  Cys  Tyr
             ——— 4a ———                                       ——— 5a ———
   ATC  AAC GTC GAA CCA GGT AAC AAC GGT GGT AAG ATC TGG GCT AGA ACC GAC TGT TAC
   TAG  TTG CAG CTT GGT CCA TTG TTG CCA CCA TTC TAG ACC CGA TCT TGG CTG ACA ATG
                              ——— 4b ———

60                                         70
   Phe  Asp  Asp  Ser  Gly  Ser  Gly  Ile  Cys  Lys  Thr  Gly  Asp  Cys  Gly  Gly  Leu  Leu  Arg
                                                                              ——— 6a ———
   TTC  GAT GAC TCT GGT TCC GGT ATC TGT AAG ACT GGT GAC TGT GGT GGT TTG TTG AGA
   AAG  CTA CTG AGA CCA AGG CCA TAG ACA TTC TGA CCA CTG ACA CCA CCA AAC AAC TCT
                              ——— 5b ———
```

TABLE 8-continued

```
                                                          EcoRI
                  80                                                   90
Cys Lys Arg Phe Gly Arg Pro Pro Thr Thr Leu Ala Glu Phe Ser Leu Asn Gln Tyr
─────────────────                           ────────────────           ──────7a──
TGT AAG AGA TTC GGT AGA CCA CCA ACC ACT TTG GCT GAA TTC TCT TTG AAC CAA TAC
ACA TTC TCT AAG CCA TCT GGT GGT TGG TGA AAC CGA CTT AAG AGA AAC TTG GTT ATG
                                    ──────6b──────

EcoRIV
                  100                                            110
Gly Lys Asp Tyr Ile Asp Ile Ser Asn Ile Lys Gly Phe Asn Val Pro Met Asn Phe
                                                           ──────8a──────
GGT AAG GAC TAC ATC GAT ATC TCC AAC ATC AAG GGT TTC AAC GTT CCA ATG AAC TTC
CCA TTC CTG ATG TAG CTA TAG AGG TTG TAG TTC CCA AAG TTG CAA GGT TAC TTG AAG
                       ──────7b──────

120                                        130
Ser Pro Thr Thr Arg Gly Cys Arg Gly Val Arg Cys Ala Ala Asp Ile Val Gly Gln
────────────────                                            ──────9a──────
TCT CCA ACC ACT AGA GGT TGT AGA GGC GTC AGA TGT GCT GCT GAC ATC GTT GGT CAA
AGA GGT TGG GCA TCT CCA ACA TCT CCG CAG TCT ACA CGA CGA CTG TAG CAA CCA GTT
                ──────8b──────

HindIII
                        140                                             150
Cys Pro Ala Lys Leu Lys Ala Pro Gly Gly Gly Cys Asn Asp Ala Cys Thr Val
                                 ──────10a──────
TGT CCA GCT AAG CTT AAG GCT CCA GGT GGT GGT TGT AAC GAC GCT TGT ACC GTT
ACA GGT CGA TTC GAA TTC CGA GGT CCA CCA CCA ACA TTG CTG CGA ACA TGG CAA
9b─────────                                                  ──────10b─────

XbaI
                       160                                       170
Phe Gln Thr Ser Glu Tyr Cys Cys Thr Thr Gly Lys Cys Gly Pro Thr Glu Tyr Ser Arg
                             ──────11a──────
TTC CAA ACT TCC GAA TAC TGT TGT ACC ACT GGT AAG TGT GGT CCA ACC GAA TAC TCT AGA
AAG GTT TGA AGG CTT ATG ACA ACA TGG TGA CCA TTC ACA CCA GGT TGG CTT ATG AGA TCT
                                                                  ──────11b──────

180                                        190
Phe Phe Lys Arg Leu Cys Pro Asp Ala Phe Ser Tyr Val Leu Asp Lys Pro Thr Thr Val
────12a────                             ────13a────
TTC TTC AAG AGA TTG TGT CCA GAC GCT TTC TCC TAC GTC TTG GAC AAG CCA ACT ACC GTC
AAG AAG TTC TCT AAC ACA GGT CTG CGA AAG AGG ATG CAG AAC CTG TTC GGT TGA TGG CAG
                 ──────12b──────                              ──────13b──────

200                                    207
Thr Cys Pro Gly Ser Ser Asn Tyr Arg Val Thr Phe Cys Pro Thr Ala
                                ──────14a──────                  XhoI
ACT TGT CCA GGT TCT TCC AAC TAC AGA GTT ACC TTC TGT CCA ACT GCC TAA TCA C
TGA ACA GGT CCA AGA AGG TTG ATG TCT CAA TGG AAG ACA GGT TGA CGG ATT ACT GAG CT
                                  ──────14b──────
```

Simultaneous integration of two gene portions into the vector containing the third, pING285, was accomplished by taking advantage of the requirement for an intact ampicillin-resistant gene in viable colonies and destroying the integrity of this gene on the two plasmids donating remaining gene portions. Thereafter, plasmids pING256, containing duplexes 1–6, and pING270, containing duplexes 7–11, were linearized with PstI and the resultant 3' single stranded regions were degraded by the action of DNA polymerase I (Klenow). After ligation, the ampicillin-resistant gene contained a frameshift which prevented expression of an active gene product. The gene portions were subsequently excised with BamHI and EcoRI for pING256 and EcoRI and XbaI for pING270. The vector which accepted the two restriction fragments (pING285, which contained oligonucleotide duplexes 12–14) was alkaline phosphatase treated to prevent closure without the phosphorylated restriction fragments from pING256 and pING270. The resulting plasmid, containing the entire synthetic thaumatin I gene, was named pING301. 50% of the colonies isolated contained the expected restriction map of the thaumatin gene. Sequence analysis demonstrated that the entire coding sequence was present.

The following example is directed to the construction of a fused gene comprising the entire thaumatin coding sequence of pING301 inserted in the proper reading frame immediately following the first 426 nucleotides of the S. typhimurium araB gene.

The following example is directed to vector constructions for expression of the thaumatin gene in yeast cells.

EXAMPLE 10

In this example, plasmid pING54 was constructed from three plasmids: pING1, the construction of which is described in Johnston, et al., *Gene*, 34, 137–145 (1985); pUC8 which is described in Messing and Viera, Gene, 19, 269–276 (1982) and is commercially available; and pING301, a plasmid containing the entire sequence for thaumatin I according to the sequence of Iyengar, et al., the construction of which is described in Example 9 above. In this construction, the pING1 plasmid was digested with XmnI restriction enzyme to yield a first fragment containing two BamHI restriction sites and a second fragment containing a unique NdeI restriction site. The second fragment was then cleaved with restriction enzyme BglI to develop a third fragment, having the ampicillin resistance gene and a PstI site, which was deleted. An ampicillin resistant fragment similar to the deleted pING1 fragment but lacking a PstI site was then isolated from pUC8 using restriction enzymes BglI and XmnI.

The pUC8 ampicillin resistance fragment was then ligated with the first and second fragments from pING1 with T4 DNA ligase to form a plasmid designated pJHL57. This plasmid was then digested with restriction enzymes BamHI and NdeI to yield a fragment containing an ampicillin resistance gene and non-contiguous portions of the first and second pING1 fragments. Plasmid pING301 was cleaved with restriction enzymes BamHI and NdeI to yield a fragment containing a sequence coding for [Asn$^{113}$] thaumatin I according to the sequence of Iyengar, et. al. The pING301 BamHI/NdeI fragment was then ligated to the BamHI/NdeI fragment from the pJHL57 to form plasmid pING54 containing the thaumatin gene.

EXAMPLE 11

In this example, the gene coding for [Asn$^{113}$] thaumatin I according to the sequence of Iyengar, et al. was changed via a site directed mutagenesis to code for an [Asp$^{113}$] thaumatin I analogue. A mutagenesis primer with the nucleotide sequence (5'-GAGAGAAGTCCATTGGAAC-3') was chemically synthesized and was passed through a Sephadex G-50 column in a 10 mM solution of triethylaminebicarbonate. The fraction containing the mutagenesis primer was then run on an HPLC C18 column using two buffer solutions, one of which was 10 mM triethylamine (buffer A), the other of which was 10 mM triethylamine and 50% acetonitrile (buffer B). The mutagenesis primer fragment eluted at a 44% concentration of buffer B. The peak fraction was collected, dried down and resuspended in 200 μl of an 80% acetic acid solution for 30 minutes at 23° C. The fraction was then spin vacuumed dry and resuspended in 200 μl of water and spin vacuumed dry a second time and resuspended in 50 μl of water. One μl of the solution (at approximately 70 μg/ml) was then treated with T4 kinase in a 10 μl volume.

At the same time, plasmid pING54, as described in Example 10, was digested with restriction enzyme XhoI, was blunt-ended with T4 DNA polymerase in the presence of all four deoxyribonucleotide triphosphates (dNTP), and was then digested with restriction enzyme BamHI to yield an approximately 630 base pair fragment encoding [Asn$^{113}$] thaumatin. The fragment was ligated into the replicative form of commercially available phage M13 mp10 (described by Messing, J., *Methods in Enzymology*, Vol. 101 pp. 20–78 (1983)) which had been digested with restriction enzyme PstI, subjected to blunt-end treatment with T4 DNA polymerase and was then cut with restriction enzyme BamHI. The M13 phage which contained the desired insert of the thaumatin gene was then designated "M13 mp10-thaumatin".

After isolation of the mutagenesis primer fragment, 1 μg of the M13 mp10-thaumatin DNA in 1 μl of solution was combined with 2 μl of the kinased primer mixture as well as 1 μl of 10×polymerization buffer comprising 70 mM Tris-HCl, pH 7.5, 70 mM MgCl$_2$, 500 mM NaCl and 9 μl H$_2$O. The solution was heated to a temperature of 65° C. for 15 minutes at which point the element of the heating block was turned off and was allowed to cool to room temperature with the tube still in it.

Primer elongation was then carried out by adding 1 μl of 0.1M DTT, 1 μl of 25 mM dNTP and 2 units of DNA Polymerase I, Klenow Fragment with 10 μl of water and incubating at 23° C. for 30 minutes. One μl of 100 mMATP and 0.5 μl T4 ligase were then added and the mixture was incubated at 15° C. for 6 hours. *E. coli* strain 71.18 cells [Gronenbron, B., *Mol. Gen. Genet.*, Vol. 148, pp. 243–250 (1976), although any F$^+$ *E. coli* strain such as JM101 (ATCC No. 33876) would be suitable] were transfected and approximately 300 plaques appeared the next day. A plaque hybridization was performed using a $^{32}$p labelled mutagenesis primer as the probe according to the published protocol [Maniatis, et al., *Molecular Cloning, A Laboratory Manual*, Cold Spring Habor Laboratory, 1982]. Washes were then conducted at 62° C. (6° C. above the melting temperature) to remove the excess probe molecules from the filter. Twelve positive hybridizing plaques were identified by autoradiography. One of the positive plaques was selected, diluted by 10$^5$ times and replated on a TYE plate comprising 15 g tryptone, 10 g yeast extract and 5 g NaCl per liter. A further hybridization was then performed and two positive plaques were selected for sequencing. Both plaques gave the desired sequence for a mutated gene coding for an [Asp$^{113}$] thaumatin I analogue. One of the phages was then designated "M13 mp10-thaumatin-D."

EXAMPLE 12

In this example, plasmids pING52 and pING58 were constructed. To express the thaumatin gene in yeast, the PGK gene from *Saccharomyces cerevisiae* was isolated from a yeast genomic bank using colony hybridization (as described in Example 7) with a 17-mer synthetic probe complementary to the published PGK promoter sequence [Dobson, et al., *Nucleic Acid Res.*, 10, 2625–2637 (1982)]. A 3 kb HindIII fragment containing the PGK gene was subcloned into *E. coli* pBR322 to generate hybrid plasmid pPGK-p. pPGK-p was thereafter digested with MboII to obtain a 218 bp MboII fragment containing the proximal end of the PGK promoter from pPGK-p. This fragment was reacted with T4 DNA polymerase to produce blunt ends and ligated to BclI-digested and blunt-ended pING250 (Example 9). The resulting plasmid, pING51, contained an MboII site re-created at only the 5' end of the PGK promoter. Plasmid pING51 was redigested with MboII, and treated with T4 DNA polymerase to produce blunt ends. After attachment of BamHI linkers at the blunt-ended MboII site, pING51 was digested with EcoRI to remove the PGK-thaumatin (portion A) sequence, which was thereafter joined to BamHI and EcoRI digested pING301. The complete thaumatin sequence was contained in the resulting plasmid, pING52.

Plasmid pING52 was digested with BamHI, filled in with T4 DNA polymerase, and then digested with EcoRI to generate a PGK promoter-thaumatin (portion A) fragment which contained a blunt end at the 5' terminus and a EcoRI sticky end at the 3' terminus. pPGK-p was digested with XbaI, treated with T4 DNA polymerase to fill in the ends, and digested with EcoRI, thereby removing a portion of the plasmid's intact PGK structural gene. The insertion of the PGK promoter-thaumatin (portion A) fragment into the digested pPGK-p formed pING55a, which thereby contained tandem PGK promoters. A deletion was generated between the duplicated promoter regions through in vivo recombination in *E. coli*, placing the intact PGK promoter immediately upstream from the 5' end of the thaumatin gene. A representative clone, designated pING56a, contained only portion A of the thaumatin gene. The PGK-thaumatin (portion A) fragment was removed from pING56a by a BamHI/EcoRI double digestion and joined to the same restriction sites in pING52, resulting in plasmid pING57 which contained the complete PGK promoter and transcriptionally active thaumatin gene on a BamHI/XhoI fragment.

To create an *E. coli*-yeast shuttle vector to receive this BamHI/XhoI fragment, plasmid pPGK-p was digested with BglII and EcoRI and treated with T4 DNA polymerase to produce blunt ends. XhoI linkers were attached, and the plasmid was religated and transformed into *E. coli* strain MC1061 to generate pING53, in which the PGK terminator was located between the XhoI and HindIII sites. A BamHI/HindIII fragment containing the PGK terminator and 190 base pairs of pBR322 DNA was then joined to the yeast- *E. coli* shuttle vector, pJDB209 [Beggs, J., "Multicopy Yeast Plasmid Vectors" in *Molecular Genetics in Yeast*, von Wettstein, et al., eds. (Copenhagen 1981)], at the BamHI and HindIII sites to create pING58. Plasmid pJDB209 harbored in host cell *E. coli* K12 strain MC1061 has been deposited with the American Type Culture Collection, 12301 Parklawn Drive, Rockville, Md. 20852 and designated ATCC 39449.

EXAMPLE 13

In this example, phage M13 mp10-thaumatin-D described in Example 11 was digested with restriction enzymes EcoRI and HindIII and ligated into the long fragment of an EcoRI and HindIII digest of pING52, a plasmid containing the entire sequence for thaumatin I according to the sequence of Iyengar, et al. and a shortened PGK promoter, the construction of which is described in Example 12 above. The resultant plasmid was designated pKS-5-2.

The pKS-5-2 plasmid was then digested with BamHI and XhoI, and the 850 base pair thaumatin coding sequence was ligated into BamHI and XhoI digested pING58, a plasmid containing a PGK terminator sequence, the construction of which is described in Example 12 above. The resultant plasmid bearing the sequence for [Asp$^{113}$] thaumatin I and a shortened PGK promoter and a PGK terminator was designated pING407.

EXAMPLE 14

In this example, the gene coding for [Asn$^{113}$] thaumatin I according to the sequence of Iyengar, et al. was changed via insertion of a manufactured gene sequence to code for lysine instead of asparagine at the 46th amino acid residue from the amino terminal end. A 12 base pair probe coding for lysine instead of asparagine with the nucleotide sequence (CAAGGGTGGTAA) was chemically synthesized as was a 20 base pair complementary fragment having active KpnI and BglII restriction sites at its ends (CATGGTTCCCAC-CATTCTAG)

Plasmid pING52 was treated with KpnI and BglII restriction enzymes and T4 ligase so as to insert the 20 base pair double stranded oligomer comprising the 12 base pair and 20 base pair strands into the thaumatin coding region and generate plasmid pING141. The pING141 clones which differ from the pING52 clones by one base pair were identified by using a colony hybridization. The 12 base sequence was used as a probe to successfully hybridize the pING141 clones and not the pING52 clones at 37° C. The clones were then sequenced to confirm the change from Asn$^{46}$ to Lys$^{46}$.

EXAMPLE 15

In this example, a procedure was carried out to recombine the mutations in the genes coding for the [Lys$^{46}$] thaumatin I analogue and the [Asp$^{113}$] thaumatin I analogue to form a gene coding for a [Lys$^{46}$, AsP$^{113}$] thaumatin I analogue with lysine at the 46th amino acid residue from the amino terminal end and aspattic acid at the 113th amino acid residue from the amino terminal and Plasmid pING141 described in example 8 above coding for the sequence of a [Lys$^{46}$] thaumatin I analogue was digested with EcoRI and HindIII to open up the thaumatin coding sequence between the glutamate residue at position 89 and the lysine residue at position 137. At the same time, phage M-13 mp10-thaumatin-D, described in example 6, and coding for an [Asp$^{113}$] thaumatin I analogue was digested with restriction enzymes EcoRI and HindIII to isolate the corresponding portion of its sequence. The M-13 mp10-thaumatin-D fragment was then ligated with T4 DNA ligase into the long fragment from the EcoRI and HindIII digest of pING141 sequence to form plasmid pKS-6 coding for a [Lys$^{46}$, Asp$^{113}$] thaumatin I analogue. The pKS-6 plasmid was purified in a colony hybridization procedure utilizing a probe with the sequence (GAGAGAAGTCCATTGGAAC).

The pKS-6 plasmid was then digested with BamHI and XhoI, and the 850 base pair thaumatin coding sequence was ligated into BamHI and XhoI digested pING58. The resultant plasmid bearing the sequence for [Lys$^{46}$, Asp$^{113}$] thaumatin I and a shortened PGK promoter sequence and a PGK terminator sequence was designated pING406.

EXAMPLE 16

In this example, plasmid pING407 coding for Asp$^{113}$] thaumatin I was transformed into *S. cerevisiae* strain AH22 [ATCC 38626]. Yeast strains carrying the plasmid were cultured in SD(−)leu medium, a synthetic complete medium consisting of nitrogen base without amino acids, 2% glucose, amino acid supplements without leucine, and purine and pyrimidine supplements, since the PGK promoter in the plasmid is constitutive when cells are grown in the presence of glucose as the sole carbon source. Single colony yeast transformants Containing plasmid pING407 were innoculated into 15 ml of SD(−) leucine broth and grown to saturation at 30° C. with vigorous shaking (A$_{600\ nm}$ approximately 2.1). The saturated cultures were precooled on ice and washed twice with PBS before lysis.

One ml of lysis buffer (20 mM Tris-Cl, 1% SDS, pH 7.2) was added to each 0.5 g of the cells prepared above and the suspension was boiled for 10 minutes to achieve cell breakage. The samples were then centrifuged at 14000×g to clarify the supernatent. This was subsequently analyzed by electrophoresis through a 15% discontinuous SDS-polyacrylamide gel (SDS-PAGE). The recombinant thaumatin was identified by comigration of a thaumatin standard and was measured by a variation of the method of Lowry. et al., *J.Biol.Chem.*, 193, 265–275 (1951) with crystalline bovine serum albumin as a standard.

Recombinant [Asp$^{113}$] thaumatin I isolated by the above procedure was in a denatured, biologically inactive form which was not sweet. The material was then subjected to the refolding procedure of U.S. Pat. No. 4,766,205 for "Method for Isolation of Recombinant Polypeptides in Biologically Active Forms," the disclosure of which is hereby incorporated by reference. A portion of the material was successfully refolded to its native conformation and was found to elicit a sweet taste sensation upon concentration.

Example 17

In this example, plasmid pING406 coding for [Lys$^{46}$, Asp$^{113}$] thaumatin I was transformed into *S. cerevisiae* strain AH22 [ATCC 38626]. Yeast strains carrying the plasmid were cultured in SD(–)leu medium, a synthetic complete medium consisting of nitrogen base without amino acids, 2% glucose, amino acid supplements without leucine, and purine and pyrimidine supplements, since the PGK promoter in the plasmid is constitutive when cells are grown in the presence of glucose as the sole carbon source. Single colony yeast transformants containing plasmid pING407 were innoculated into 15 ml of SD(–) leucine broth and grown to saturation at 30° C. with vigorous shaking ($A_{600\ nm}$ approximately 2.1). The saturated cultures were precooled on ice and washed twice with PBS before lysis.

One ml of lysis buffer (20 mM Tris-HCl, 1% SDS, pH 7.2) was added to each 0.5 g of the cells prepared above and the suspension was boiled for 10 minutes to achieve cell breakage. The samples were then centrifuged at 14000×g to clarify the supernatent. This was subsequently analyzed by electrophoresis through a 15% discontinuous SDS-polyacrylamide gel (SDS-PAGE). The recombinant thaumatin was identified by comigration of a thaumatin standard and was measured by a variation of the method of Lowry. et al., *J.Biol.Chem.*, 193, 265–275 (1951) with crystalline bovine serum albumin as a standard.

Recombinant [Lys$^{46}$, Asp$^{113}$] thaumatin I isolated by the above procedure was in a denatured, biologically inactive form which was not sweet. The material was then subjected to the refolding procedure of U.S. Pat. No. 4,766,205 the disclosure of which is hereby incorporated by reference. A portion of the material was successfully refolded to its native conformation and was found to elicit a sweet taste sensation without concentration.

Numerous modifications and variations in the invention are expected to occur to those skilled in the art upon consideration of the foregoing description. As one example, while the foregoing illustrated example is directed to site-directed mutagenesis of a DNA sequence to alter a 5'-AAC-3' codon specifying asparagine to a 5'-GAC-3' codon specifying aspattic acid, an [Asp$^{113}$] thaumatin I gene of the invention could be developed wherein the pertinent aspartic acid residue was encoded by 5'-GAT-3'. Consequently, only such limitations as appear in the following claims should be placed upon the invention.

What is claimed is:

1. A purified and isolated DNA sequence encoding the amino acid sequence of sweet-tasting (Asp$^{113}$) Thaumatin I wherein the DNA sequence is a manufactured gene and the base sequence comprises one or more codons selected from among alternative codons specifying the same amino acid on the basis of preferential expression characteristics of the codon in *Saccharomyces cerevisiae*.

2. A purified and isolated DNA sequence encoding the amino acid sequence of sweet-tasting (Lys$^{46}$, Asp$^{113}$) Thaumatin I wherein the DNA sequence is a manufactured gene and the base sequence comprises one or more codons selected from among alternative codons specifying the same amino acid on the basis of preferential expression characteristics of the codon in *Saccharomyces cerevisiae*.

3. A microorganism transformed with a vector comprising a gene selected from the group of genes encoding the amino acid sequences of sweet-tasting (Asp$^{113}$) Thaumatin I and sweet-tasting (Lys$^{46}$, Asp$^{113}$) Thaumatin I which is a *Saccharomyces cerevisiae* microorganism.

* * * * *

UNITED STATES PATENT AND TRADEMARK OFFICE
CERTIFICATE OF CORRECTION

PATENT NO. : 5,464,770

DATED : November 7, 1995

INVENTOR(S) : WEICKMANN ET AL.

It is certified that error appears in the above-identified patent and that said Letters Patent is hereby corrected as shown below:

Column 4, line 20, "acid the" should be --acid in the--.

Column 4, line 39, "following, detailed" should be --following detailed--.

Column 5, line 36, "of crowned" should be --of co-owned--.

Column 7, line 23, "as aspattic" should be --as aspartic--.

Column 9, Table 5, insert --XbaI-- above "SstI" at the third column in the row beginning with "12a and 12b".

Column 11, Table 6, at pair 3, --SstI-- should be above "5'-CC".

Column 11, Table 6, pair 12, "XbaI" should be --IbaI--.

Column 15, line 30, "endonucleaseenzyme" should be --endonuclease enzyme--.

Column 16, line 31, "mMATP" should be --mM ATP--.

Column 16, line 52, "instep (b)" should be --in step (b)--.

Column 17, Table 8, the line "—1a—" should extend above "GATC (xxx)$_6$ GTT A".

Columns 17-18, Table 8, the line "—2a—" should extend above "GG GCT (xxx)$_6$ GCT G".

Columns 17-18, Table 8, the line "—3a—" should extend above "CC GGT (xxx)$_3$ TTG A".

Columns 17-18, Table 8, the line "—4a—" should extend above "G ACC (xxx)$_6$ AAC AA".

UNITED STATES PATENT AND TRADEMARK OFFICE
CERTIFICATE OF CORRECTION

PATENT NO. : 5,464,770

DATED : November 7, 1995

INVENTOR(S) : WEICKMANN ET AL.

Page 2 of 4

It is certified that error appears in the above-identified patent and that said Letters Patent is hereby corrected as shown below:

Columns 17-18, Table 8, the line "—5a—" should extend above "AG ATC (xxx)$_8$ GAT G".

Columns 18-19, Table 8, the line "—6a—" should extend above "T GAC (xxx)$_{10}$ GGT".

Columns 19-20, Table 8, the line "—7a—" should extend above "GAA (xxx)$_8$ GAC".

Columns 19-20, Table 8, the line "—8a—" should extend above "GGT (xxx)$_9$ ACC".

Columns 19-20, Table 8, the line "—9a—" should extend above "C GTC" (xxx)$_6$ GTT".

Columns 19-20, Table 8, the line "—10a—" should extend above "AAG (xxx)$_8$ AAC".

Column 19, Table 8, the line "—11a—" should extend above "TCC (xxx)$_9$ GGT".

Columns 19-20, Table 8, the line "—12a—" should extend above "TCT (xxx)$_6$ TTG TG".

Columns 19-20, Table 8, the line "—13a—" should extend above "GCT (xxx)$_6$ GAC AA".

Columns 19-20, Table 8, the line "—14a—" should extend above "GGT (xxx)$_8$ TGT C".

Columns 17-18, Table 8, the line "—1b—" should extend below "CTT (xxx)$_8$ CAA A".

Column 17, Table 8, the line "—2b—" should extend below "CA CTG (xxx)$_3$ CTG C".

Columns 17-18, Table 8, the line "—3b—" should extend below "CT GTT (xxx)$_6$ AGG AC".

Columns 17-18, Table 8, the line "—4b—" should extend below "T CCA (xxx)$_6$ TAG A".

UNITED STATES PATENT AND TRADEMARK OFFICE
CERTIFICATE OF CORRECTION

PATENT NO.    :  5,464,770
DATED         :  November 7, 1995
INVENTOR(S)   :  WEICKMANN ET AL.

It is certified that error appears in the above-identified patent and that said Letters Patent is hereby corrected as shown below:

Columns 17-18, Table 8, the line "—5b—" should extend below "TG AAG (xxx)$_9$ TGA CC".

Columns 19-20, Table 8, the line "—6b—" should extend below "TCT (xxx)$_{10}$ AAG".

Columns 19-20, Table 8, the line "—7b—" should extend below "CCA (xxx)$_9$ TTC".

Column 19, Table 8, the line "—8b—" should extend below "AGA (xxx)$_6$ TCT CC".

Columns 19-20, Table 8, the line "—9b—" should extend below "CTG (xxx)$_8$ GAA".

Columns 19-20, Table 8, the line "—10b—" should extend below "CCA (xxx)$_9$ TGA".

Columns 19-20, Table 8, the line "—11b—" should extend below "TTC (xxx)$_7$ TCT".

Column 19, Table 8, the line "—12b—" should extend below "C TCT (xxx)$_3$ CTG".

Columns 19-20, Table 8, the line "—13b—" should extend below "G AAC (xxx)$_8$ GGT".

Columns 19-20, Table 8, the line "—14b—" should extend below "GG AAG (xxx)$_6$ GAG CT".

Column 22, line 11, "mMATP" should be --mM ATP--.

Column 22, line 18, "$^{32}$p" should be --$^{32}$P--.

Column 24, line 18, "[Lys$^{46}$, AsP$^{113}$]" should be --[Lys$^{46}$, Asp$^{113}$]--.

Column 24, line 20, "and aspattic" should be --and aspartic--.

UNITED STATES PATENT AND TRADEMARK OFFICE
CERTIFICATE OF CORRECTION

PATENT NO. : 5,464,770
DATED : November 7, 1995
INVENTOR(S) : WEICKMANN ET AL.

It is certified that error appears in the above-identified patent and that said Letters Patent is hereby corrected as shown below:

Column 24, line 22, "example 8" should be --example 14--.

Column 24, line 27, "example 6" should be --example 11--.

Column 24, line 46, "for Asp$^{113}$]" should be --for [Asp$^{113}$]--.

Column 26, line 15, "aspattic acid," should be --aspartic acid,--.

Signed and Sealed this

Fifth Day of November, 1996

Attest:

BRUCE LEHMAN

Attesting Officer     Commissioner of Patents and Trademarks